United States Patent [19]
Hashizume et al.

[11] Patent Number: 5,320,939
[45] Date of Patent: Jun. 14, 1994

[54] MEASURING APPARATUS OF TWO COMPONENTS USING ENZYME ELECTRODES AND THE MEASURING METHOD THEREOF

[75] Inventors: Yoshio Hashizume, Kakogawa; Ryuzo Hayashi, Higashiosaka; Akio Kariyone, Kyoto, all of Japan

[73] Assignee: Kanzaki Paper Manufacturing Co., Ltd., Tokyo, Japan

[21] Appl. No.: 953,294

[22] Filed: Sep. 30, 1992

Related U.S. Application Data

[63] Continuation of Ser. No. 443,162, Nov. 30, 1989, abandoned.

[30] Foreign Application Priority Data

Nov. 30, 1988 [JP] Japan .................. 63-302424

[51] Int. Cl.$^5$ .............................................. C12Q 1/00
[52] U.S. Cl. .................................. 435/4; 435/288; 435/291; 435/817; 422/68.1; 204/403
[58] Field of Search .............. 435/4, 817, 291, 288; 204/403; 422/68.1

[56] References Cited

U.S. PATENT DOCUMENTS

| | | | |
|---|---|---|---|
| 3,542,662 | 4/1967 | Hicks et al. | 204/195 |
| 3,707,455 | 12/1972 | Derr et al. | 204/195 P |
| 4,005,002 | 1/1977 | Racine et al. | 204/195 P |
| 4,431,507 | 2/1984 | Nankai et al. | 204/403 |
| 5,158,868 | 10/1992 | Bergkuist et al. | 435/4 |

FOREIGN PATENT DOCUMENTS 0216946 12/1983 Japan .

OTHER PUBLICATIONS

"Determination of Substrate Concentrations by a Computerized Enzyme Electrode" J. P. Kernevez et al., Biotechnology, vol. XXV, pp. 845–855 (1983).

*Primary Examiner*—James C. Housel
*Assistant Examiner*—Lien Tran
*Attorney, Agent, or Firm*—Wenderoth, Lind & Ponack

[57] ABSTRACT

In a two-substrate measuring apparatus employing a first enzyme electrode for responding only to a first substrate to be measured and a second enzyme electrode for responding to both first and second substrates to be measured, in which the same enzymatic reactions are used for forming detectable substances and the substances to be finally detected by the electrodes are identical, when calculating the calibration curve for the second substrate to be measured, the output portion due to traces of the first substrate contained in the second substrate to be measured is removed, so that the second substrate is measured at a high sensitivity and high accuracy.

4 Claims, 6 Drawing Sheets

MEASURING APPARATUS OF TWO COMPONENTS USING ENZYME ELECTRODES AND THE MEASURING METHOD THEREOF

This application is a continuation of now abandoned application Ser. No. 07/443,162, filed on Nov. 30, 1989.

BACKGROUND OF THE INVENTION

1. Field of the Invention

The present invention relates to an apparatus and method using enzyme electrodes for simultaneously measuring the concentration of two substrates such as glucose and sucrose in a liquid, and more particularly to improvements in the measuring apparatus and method wherein the same enzymatic reaction for forming a detectable substance occurs in each of a pair of electrodes, and the substance to be finally detected by each electrode is identical.

2. Description of the Prior Art

Enzyme electrodes are excellent in readiness and promptness, and have come to be used widely in various fields including clinical analysis, food analysis and environmental analysis.

Recently, in particular, great efforts are concentrated in the development of simultaneously measuring apparatus capable of measuring the concentration of two different substances using enzyme electrodes, and such simultaneous measuring apparatus for measuring, for example, glucose and uric acid (see Japanese Laid-open Patent Application No. 62-24142), lactic acid and pyruvic acid (see Japanese Laid-open Patent Application No. 62-5172), and others have been introduced, in which each of the employed enzymes function as the catalyst for a reaction with a specific object of measurement.

An apparatus for measuring the concentration of two substrates simultaneously was also disclosed by the present inventors, wherein the same enzymatic reaction for forming or consuming a detectable substance occurs in each of a pair of electrode, and the substance to be finally detected by each electrode is identical (see Japanese Laid-open Patent Application No. 64-69944, EP0310824).

A measuring method of sucrose is disclosed, in which the sucrose is hydrolyzed by invertase into fructose and α-D-glucose, and α-D-glucose is converted into β-D-glucose by mutarotase, and then β-D-glucose is oxidized by glucose oxidase to produce an electrode active substance of hydrogen peroxide, which is detected electrochemically (C. Bertrand, P. R. Coulet, D. C. Gautheron, Anal. Chim. Acta, 126, 23–34, 1981). On the other hand, to measure the concentration of glucose, the glucose is oxidized by glucose oxidase, and the produced hydrogen peroxide is electrochemically detected. That is, both in the measurement of sucrose and the measurement of glucose, the oxidation of glucose is a common reaction to produce an electrode active substance, and the substance detected by the electrode is hydrogen peroxide.

Therefore, the present inventors disclosed the method to measure simultaneously glucose and sucrose by using enzyme electrodes. The concentration of glucose is determined from the output voltage detected by the enzyme electrode having immobilized glucose oxidase. To measure the sucrose concentration, on the other hand, the enzyme electrode for detecting both glucose and sucrose having immobilized glucose oxidase, mutarotase and invertase is set in a flow type measuring apparatus. By using the previously detected concentration of glucose, the contribution portion of the glucose initially contained in the sample is calculated from the preliminarily calibrated value, concerning the enzyme electrode having immobilized glucose oxidase, mutarotase and invertase, and this value is subtracted from the output current value to determine the sucrose concentration.

That is, generally, the concentrations of two components are measured by the following methods.

Calibration means 1

First of all, using standard solutions of a first substrate to be measured at several concentrations, output currents are measured by a first enzyme electrode and a second enzyme electrode.

In the specification herein, the first substrate to be measured refers to a substance which forms by enzymatic reaction a detectable substance by the electrode. The second substrate to be measured, which is mentioned later, refers to a substance which does not produce an electrode detectable substance directly by the above mentioned enzymatic reaction, but is capable of producing the first substrate to be measured by different enzymatic reactions.

Furthermore, the first enzyme electrode is an electrode having immobilized an enzyme catalyzing the reaction to produce an electrode detectable substance from the first substrate to be measured. The second enzyme electrode is an electrode having an immobilized enzyme catalyzing the reaction to produce the first substrate to be measured from the second substrate to be measured, and an immobilized enzyme catalyzing the reaction to produce an electrode detectable substance from the first component to be measured.

In amperometry, the concentration and output current are in a proportional relationship. From the concentrations and the output current in the first enzyme electrode, a formula (1) (used as a first calibration curve a determination of the first substrate to be measured, as shown in FIG. 1 (1)) is obtained.

$$d1 = B1 \times c1 + A1 \qquad (1)$$

where c1: concentration of the first substrate to be measured d1: output current of the first enzyme electrode corresponding to the first substrate to be measured A1, B1: constants of calibration curve corresponding to the first substrate to be measured of the first enzyme electrode Likewise, from the concentrations and output current in the second enzyme electrode, a formula (2) (used as a second calibration curve for detecting the output current in the second enzyme electrode of the first substrate to be measured, as shown in FIG. 1 (2)) is obtained.

$$d2 = B2 \times c1 + A2 \qquad (2)$$

where c1: concentration of the first substrate to be measured d2: output current by the first substrate to be measured of second enzyme electrode A2, B2: constants of calibration curve corresponding to the first substrate to be measured of the second enzyme electrode Next, by measuring the standard solution of the second substrate to be measured at several concentrations by the second enzyme electrode, from the concentrations and the output current in the second enzyme electrode, a formula (3) (used as a third calibration curve for determination of the second substrate to be measured, as shown in FIG. 1 (3)) is obtained.

$$d3 = B3 \times c2 + A3 \quad (3)$$

where c2: concentration of the second substrate to be measured d3: output current by the second substrate to be measured of the second enzyme electrode A3, B3: constants of calibration curve corresponding to the second substrate to be measured of the second enzyme electrode

Determination means 1

Measuring a sample solution containing the first substrate to be measured an the second substrate to be measured, both of unknown concentration, by two enzyme electrodes, the output current d1 attributable to the first substrate to be measured is obtained in the first enzyme electrode, and the output current d23 attributable to both the first substrate to be measured and the second substrate to be measured is obtained in the second enzyme electrode.

The concentration c1 of the first substrate to be measured is obtained by putting the output current d1 in the first enzyme into formula (1), as shown below in formula (a).

$$c1 = (d1 - A1)/B1 \quad (a)$$

(See FIG. 1 (1).)

Next, the concentration of the second substrate to be measured is obtained in the following sequence. The output current of the second enzyme electrode which is attributable to the first substrate is calculated from the formula (2) and is obtained as correction value d2 as shown in formula (b) (see FIG. 1 (2)), and this correction value d2 is subtracted from the output current d23 obtained in the second enzyme electrode to obtain d3 (the current purely attributable to the second substrate to be measured) as shown below in formula (c), and this value is put into formula (3) to obtained the desired concentration as shown below in formula (d) (see FIG. 1 (3)).

$$d2 = \{B2 \times (d1 - A1)/B1\} + A2 \quad (b)$$

$$d3 = d23 - d2 \quad (c)$$

$$c2 = (d3 - A3)/B3 \quad (d)$$

The standard solution to be used in plotting the calibration curve is required to be a solution of only a pure single component with a known concentration, but when measuring, for example, glucose and sucrose simultaneously as mentioned above, glucose is often contained as an impurity in the standard solution of sucrose. In the second enzyme electrode, a small current derived from the glucose contained in the sucrose standard solution is obtained, and therefore sucrose, which is second substrate to be measured, cannot be measured accurately.

Actually in a system where the substances to be finally detected by the electrodes are identical, the first substrate to be measured is often contained as an impurity in the standard solution of the second substrate to be measured, and it is extremely difficult to remove this impurity or to detect its content in advance, and since the substance used as the standard solution gradually produces impurities little by little as the time passes (for example, sucrose produces glucose), it is practically impossible to remove or detect the impurities preliminarily. Therefore, in the measuring method of the prior art, the correct concentration of the second substrate to be measured cannot be obtained. This problem becomes more serious when the sensitivity of the measuring apparatus is higher.

Presented hereabove is the measurement of a coexistent system of sucrose and glucose, and similar problems exist in simultaneous methods of measuring two substrates using enzyme electrodes producing the same electrode active substances by the same final enzymatic reactions, for example, the measurement of a maltose-glucose coexistent system, an esterified and free cholesterol coexistent system, and the like.

SUMMARY OF THE INVENTION

It is hence a primary object of the invention to present a apparatus and measuring method for determining the concentration of two substrates in a solution at a high accuracy by solving the above-discussed problems when measuring two substrates having the same final enzymatic reaction for producing or consuming electrode active substances.

To achieve the above object, the measuring apparatus of the present invention comprises an apparatus for measuring the concentration of a substrate A and substrate B in a solution, said apparatus comprising: a first enzyme electrode for responding only to said substrate A, and a second enzyme electrode for responding to both said substrate A and said substrate B, both enzyme electrodes having an enzyme common in an enzymatic reaction for forming an identical detectable substance at said electrodes, each of said electrodes in contact with the solution containing substrates A and/or B and each of said electrodes comprising a conductive base and an immobilized enzyme which catalyzes a reaction for forming said detectable substance, and further comprising a means for calculating a calibration curve of said substrate B by (i) calculating an output due to substrate A, which is an impurity in a standard solution containing a known amount of substrate B, in said second enzyme electrode by using the relationship of the output values of both enzyme electrodes when in contact with another standard solution containing a known amount of substrate A, and (ii) subtracting said contribution portion of substrate A from the output of said second enzyme electrode wherein contact with said standard solution containing a known amount of substrate B.

The present invention also presents a measuring apparatus which comprises:

an apparatus for measuring the concentration of a substrate A and a substrate B in a solution, said apparatus comprising:

a. a first enzyme electrode for responding only to said substrate A:

b. a second enzyme electrode for responding to both said substrate A and said substrate B, each of said electrodes in contact with the solution containing substrates A and/or B and each of said electrodes comprising a conductive base and immobilized enzyme which catalyzes a reaction for forming a detectable substance and for providing an output level corresponding thereto;

c. a first memory for storing a first calibration curve for expressing the relationship between the concentration of said substrate A and said output level of said first enzyme electrode;

d. a second memory for storing a second calibration curve for expressing the relationship between the concentration of said substrate A and said output level of said second enzyme electrode;

e. a processing means and a third memory for storing a third calibration curve for expressing the relationship between the concentration of said substrate B and the output level of said second enzyme electrode calculated by said processing means;

f. said processing means calculating said third calibration curve on the basis of the output levels of said second enzyme electrode of said substrate B obtained by changing the concentration of said substrate B in standard solutions, and repeating the processing in the following sequence of f1 to f4;

f1. detecting the output levels attributable to a standard solution in said first enzyme electrode and said second enzyme electrode, wherein said standard solution contains said substrate A and said substrate B with a known concentration of said substrate B;

f2. calculating the concentration of said substrate A on the basis of the detected output level in said first enzyme electrode and said first calibration curve stored in said first memory;

f3. calculating the output level in said second enzyme electrode of said substrate A on the basis of the calculated concentration of said subtrate A and said second calibration curve stored in said second memory;

f4. calculating the output level in said second enzyme electrode of said substrate B by subtracting the calculated output level in said second enzyme electrode of said substrate A from the output level in said second enzyme electrode of said standard solution; and g. another processing means for calculating the concentrations of said substrate A and substrate B in a solution using said first, second and third calibration curves;

The invention also relates to a measuring method comprising:

a method of measuring the concentration of a substrate A and a substrate B in a solution, using a first enzyme electrode for responding only to the substrate A, and a second enzyme electrode for responding to both substrate A and substrate B, said method comprising:

a step of calculating a first calibration curve for expressing the relationship between the concentration of substrate A and an output level of the first enzyme electrode;

a step of calculating a second calibration curve for expressing the relationship between the concentration of substrate A and an output level of the second enzyme electrode;

a step of preparing a standard solution for measurement by the first and second enzyme electrodes, the standard solution containing both substrate A and substrate B, with a known concentration of substrate B;

a step of determining the concentration of substrate A contained in the standard solution by using the output level of the first enzyme electrode to the standard solution and the first calibration curve;

a step of determining the output level of the second enzyme electrode of substrate A contained in the standard solution by using the concentration of substrate A and the second calibration curve;

a step of determining the output level of the second enzyme electrode of substrate B, by subtracting the output level of the second enzyme electrode of substrate A from the output level of the second enzyme electrode;

a step of calculating a third calibration curve for expressing the relationship between the concentration of substrate B and the output level of the second enzyme electrode, by varying the concentration of substrate B in the standard solution, and repeating the procedure in the sequence of the previous four steps, and a step of determining the concentrations of substrate A and substrate B on the basis of the first, second and third calibration curves.

In the present invention, the first substrate to be measured delivers outputs to both the first and second electrodes. Indicating the output in the first electrode of the first substrate to be measured with a concentration c to be p1 and the output in the second electrode to be p2, the relationship $$c = f(p1) \tag{A}$$

$$p2 = g(p1) \tag{B}$$

is determined by measuring the standard solution of the first substrate to be measured, wherein f( ) and g( ) denote that c and p2 are expressed as a function of p1. If the second substrate to be measured is pure, no output is given to the first electrode, but if the first substrate to be measured is contained as an impurity, a current of p1' is delivered from this first substrate to be measured to the first electrode. Putting this p1' into formula (B), the output p2' of the second electrode due to the impurity will be calculated. Therefore, when p2' is subtracted from the output of the second electrode of the standard solution of the second substrate to be measured, the second electrode output which is purely attributable to the second substrate to be measured is obtained, so that, unlike the prior art, a very accurate calibration curve of the second substrate to be measured is calculated. In the conventional method, the output containing the error of p2' attributed to the second substrate in the standard solution was directly taken as the output of the second substrate to be measured in the second electrode, and the concentration of the second substrate to be measured was determined by the calibration curve containing the above error and the value obtained by subtracting the output attributed to the first substrate to be measured, said output obtained by formula (B), from the output of the second electrode, in a measurement of a sample containing first and second substrate to be measured. Hence, the measured concentration was smaller than its actual value. By contrast, in the present invention, since the portion of the output due to the impurity is eliminated in the calculation of the calibration curve for the second substrate to be measured as stated above, a correct concentration of the second substrate to be measured is obtained.

In other words, according to the present invention, in the two-substrate measuring apparatus comprising a first enzyme electrode for responding only to the first substrate to be measured and a second enzyme electrode for responding to both the first substrate to be measured and the second substrate to be measured, both of said electrodes contain an identical enzyme and the enzymatic reactions for forming electrode detectable substances are identical, and the substances to be finally detected by the electrodes are identical, and any determination error due to the first substrate to be measured which is a impurity in the second substrate to be measured does not occur, and therefore a measurement of high sensitivity and high accuracy is realized.

DETAILED DESCRIPTION OF THE PREFERRED EMBODIMENTS

The preferred embodiments of the present invention are described below in detail with reference to the drawings attached hereto.

Figure 1:
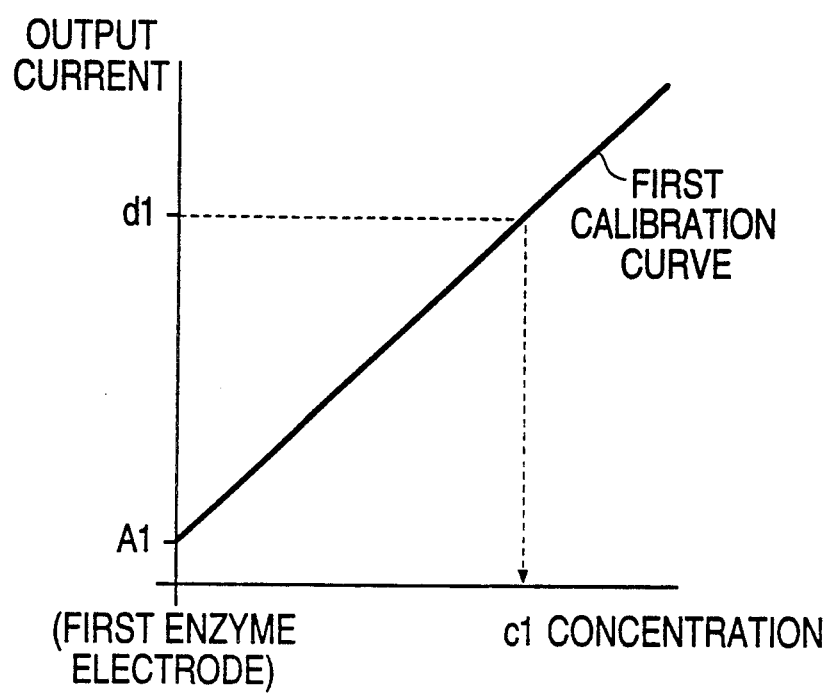
FIGS. 1(1)–1(3) are diagrams showing calibration curves used in a conventional two-substrate measuring apparatus.
Figure 2:
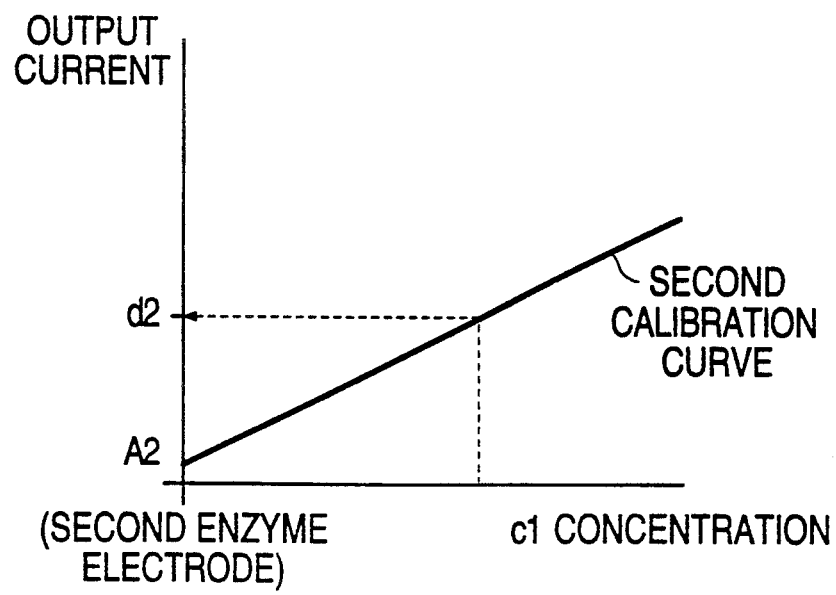
FIG. 2 is a system diagram showing an example of a two-substrate measuring apparatus of the present invention.

FIG. 2 is a system diagram showing an example of a two-substrate measuring apparatus of the present invention. This embodiment shows a flow type, in which a buffer solution 1 is supplied through a pump 2, the to be measured is injected from an injector 3, and is sent out into a drain trap 7 from a first enzyme electrode 4 through a mixing coil 5 and a second enzyme electrode 6.

To each electrode, a voltage is supplied by a potentiostat 8, and a current output based on each substrate to be measured is obtained, and this information is sent to an arithmetic processing unit 9 by means for generally converting trace current into a digital quantity such as current amplification and by digitizing the output current with an A/D converter, and the operation for the determination of the calibration curves and concentration is executed, and the result is delivered to a display or printing output unit 10. In order to explain the operation of the present invention, a first memory, second memory and third memory are described separately, but these memories may correspond to specific addresses of the same random access memory.

By diluting the sample, for example, by intervening a mixing coil between the first enzyme electrode and the second enzyme electrode, the proportional range of the second enzyme electrode is expanded, and the two substrates may be measured more accurately even if the concentration is very high (refer to Japanese Laid-open Patent Application No. 64-69944, EP0310824).

As detecting measurement methods, in addition to the amperometric method mentioned above, a potentiometric method and a thermal measurement method (to measure the changes in enthalpy due to enzymatic reaction) may be possible, but considering the dynamic range and response speed of these methods, the amperometric method is most preferable.

In the present invention, the calibration means in the arithmetic processing unit 9 may be calibrated in the procedure shown below, and thereafter the sample of unknown concentration is measured in the procedure also shown below.

Calibration means 2

First of all, output levels of a standard solution of the first substrate to be measured at several concentrations are measured by the first enzyme electrode and second enzyme electrode.

Figure 3:
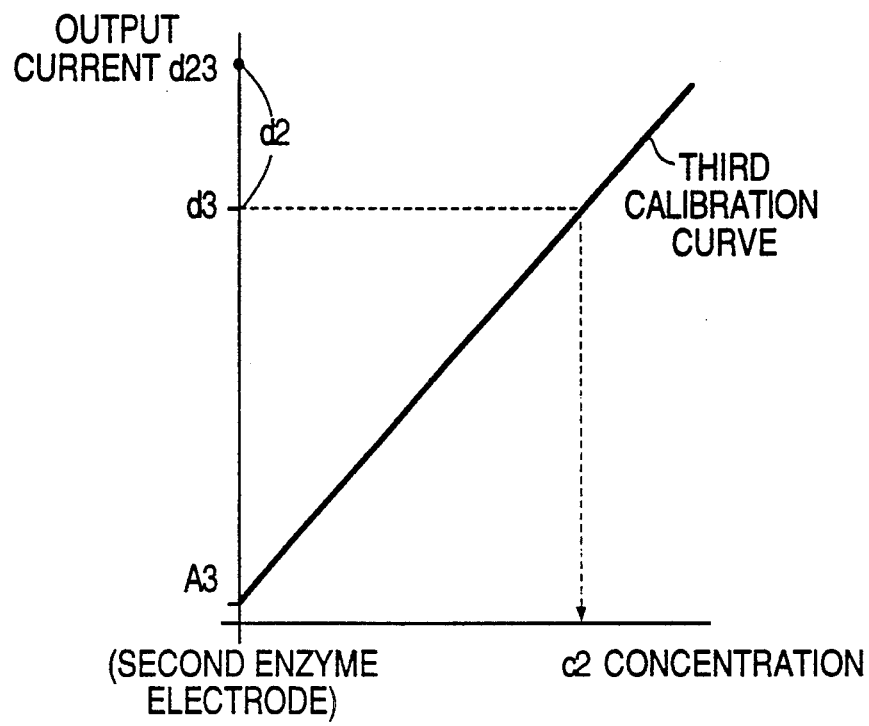
FIGS. 3(1)–3(3) are diagrams showing calibration curves used in a two-substrate measuring apparatus of the present invention.
Figure 5:
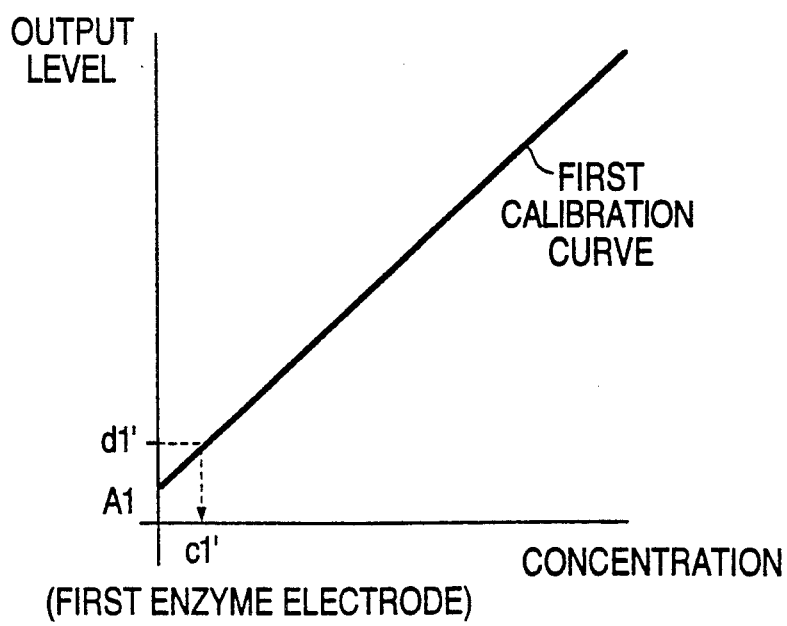
Figure 4:
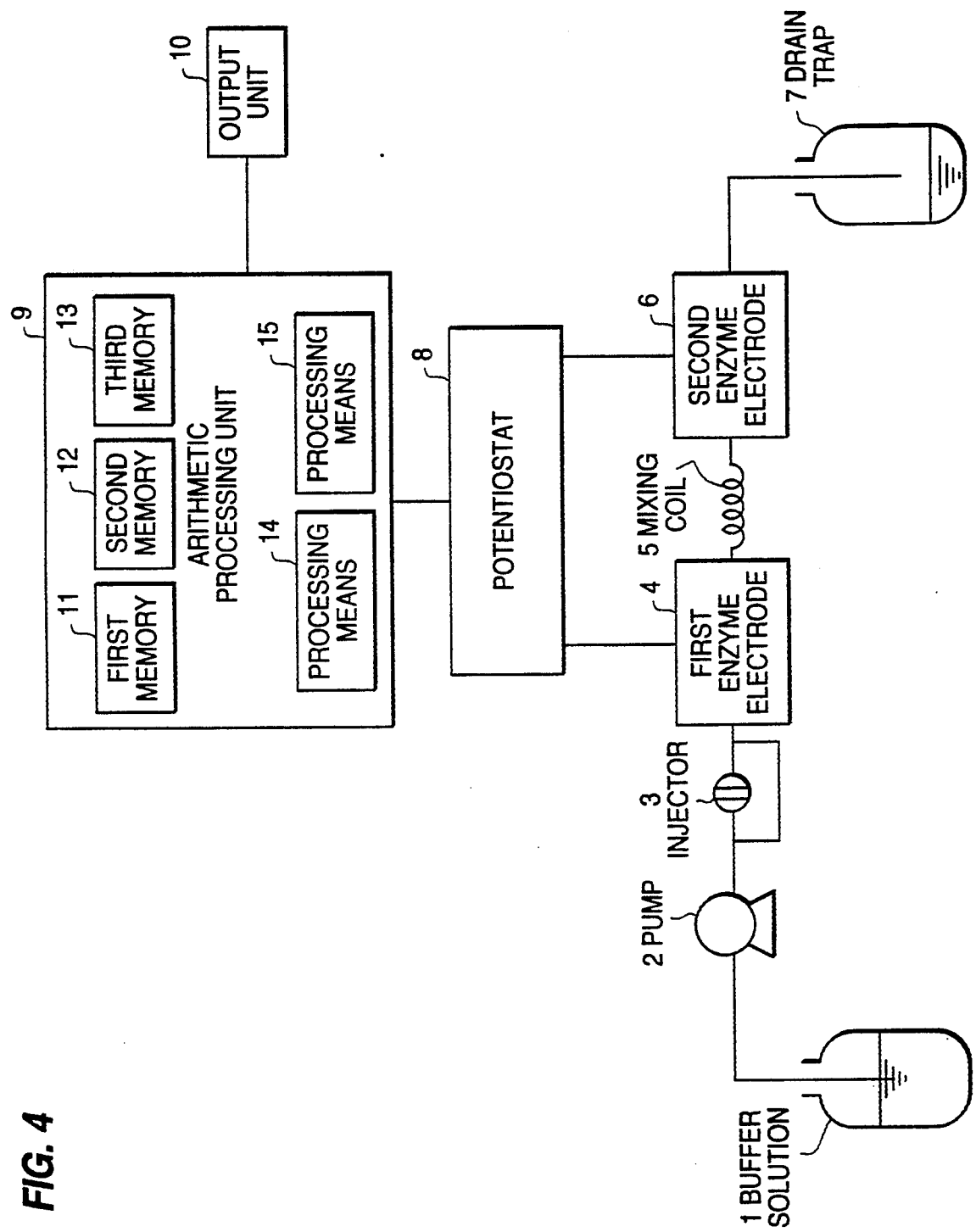
FIGS. 4(1) and 4(2) together form a flowchart showing an arithmetic processing unit of the system shown in FIG. 2.
Figure 6:
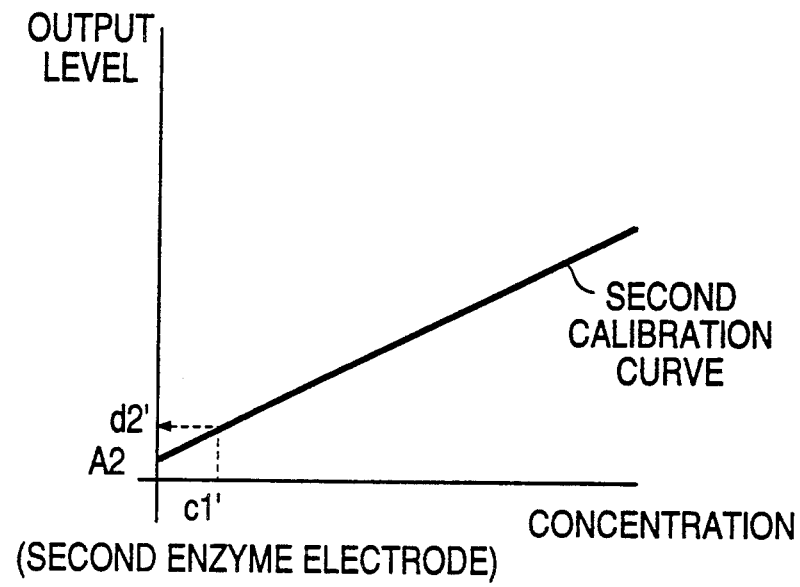
Figure 7:
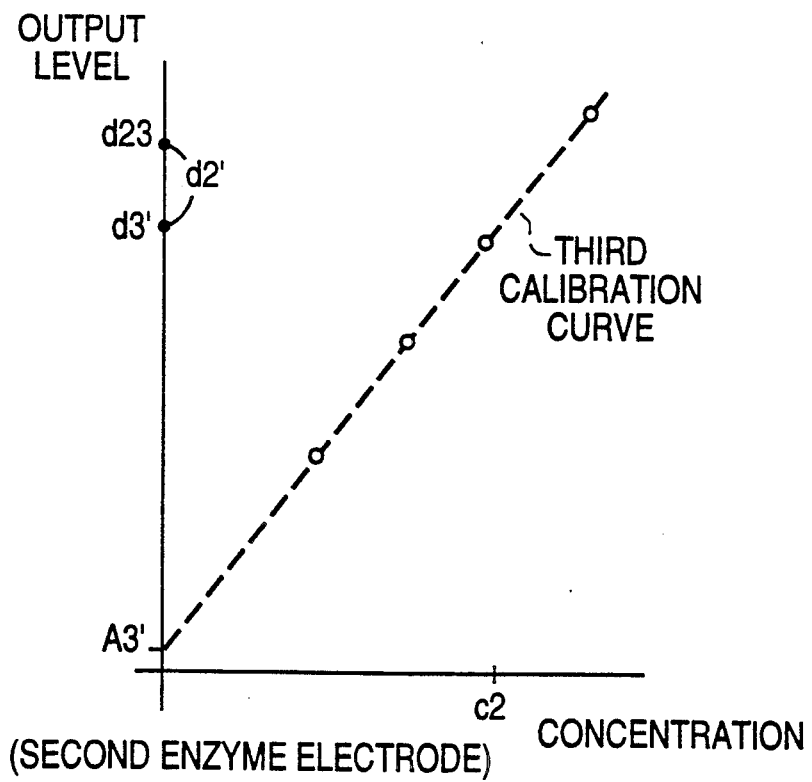
Figure 8A:
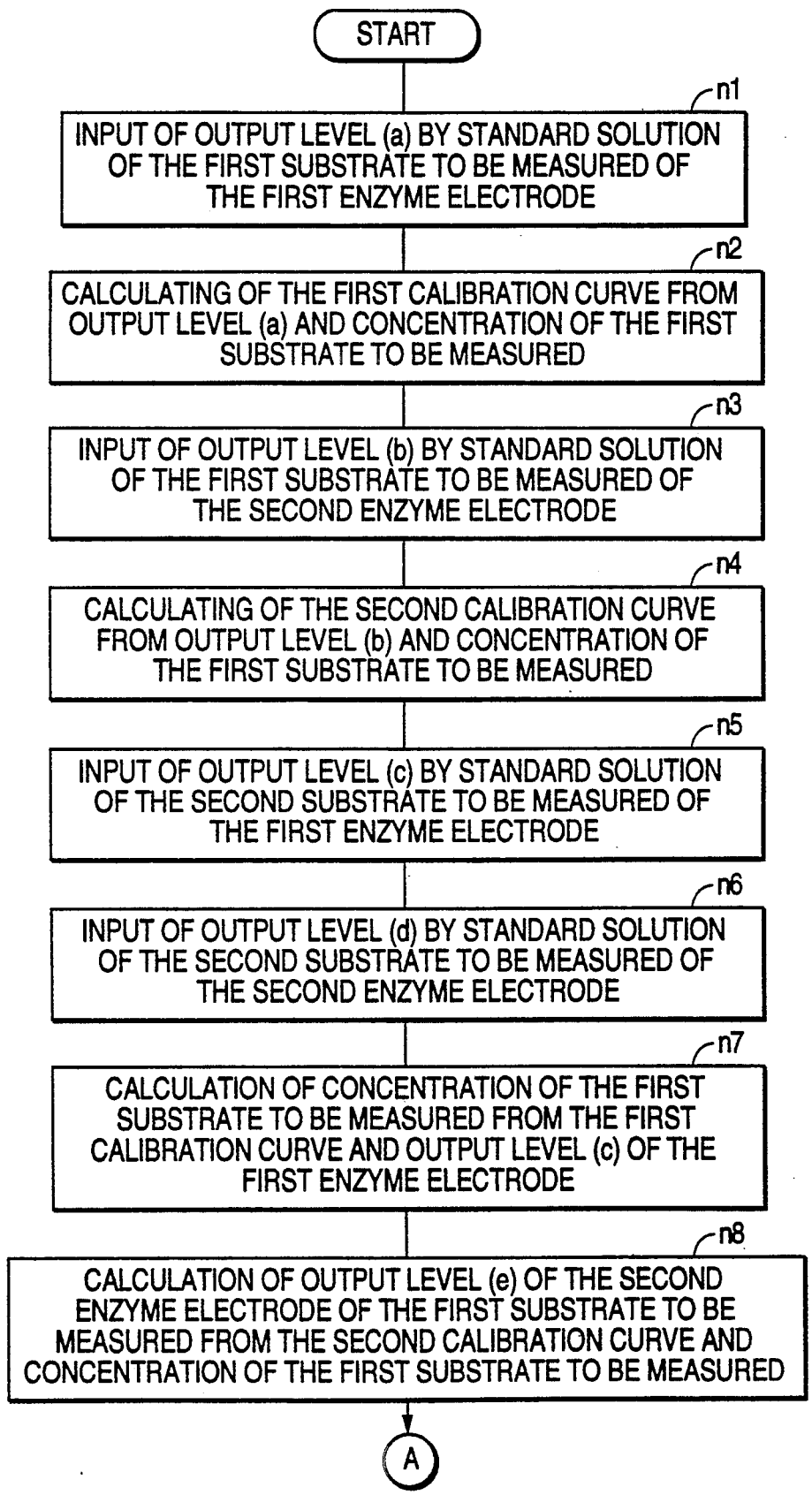
Figure 8B:
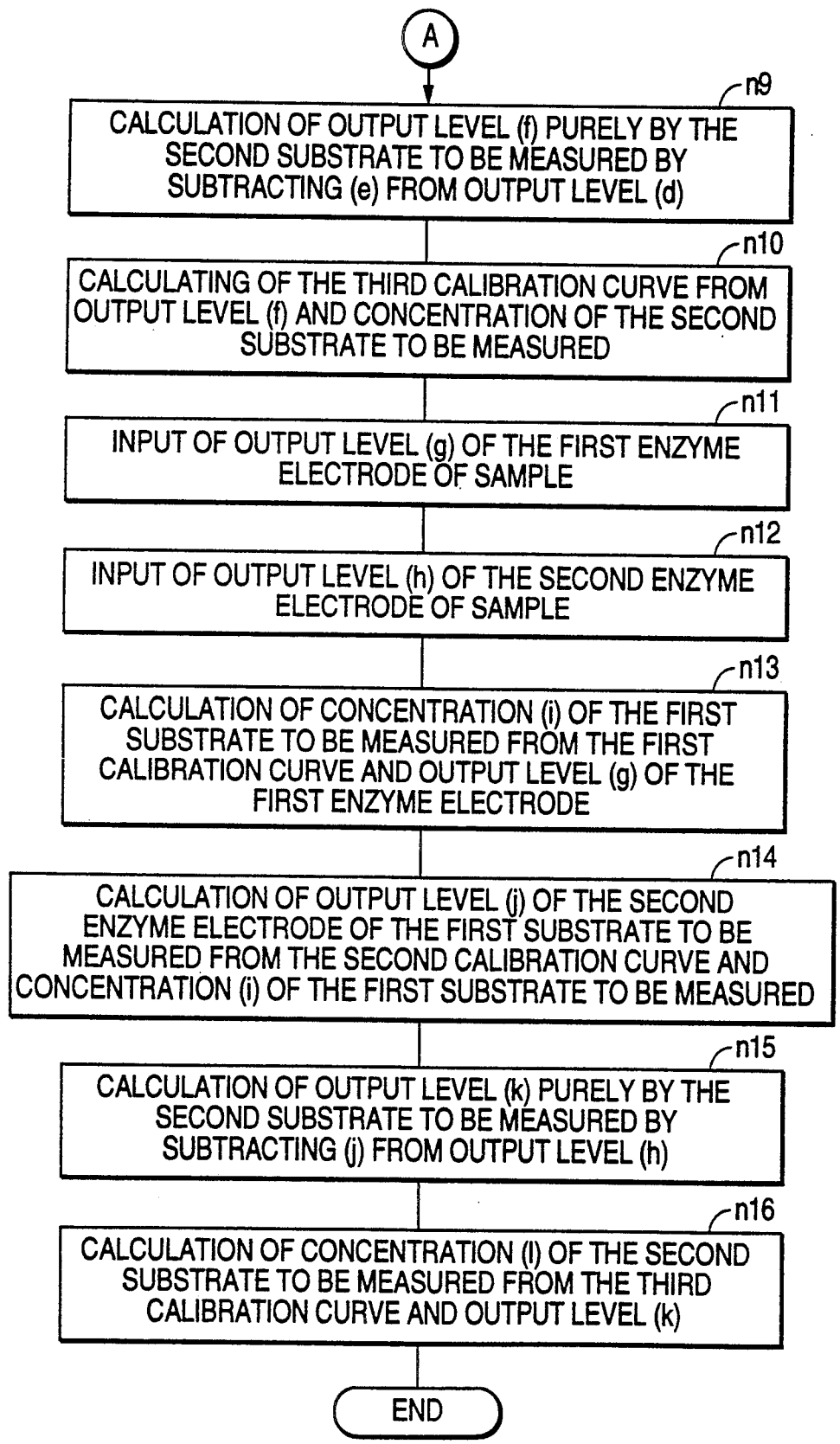

From the concentrations and the output levels in the first enzyme electrode, formula (4) (used as a first calibration curve for determination of the first substrate to be measured, as shown in FIG. 3 (1)) is obtained.

$$d1 = B1 \times c1 + A1 \tag{4}$$

where
- $c1$: concentration of the first substrate to be measured
- $d1$: output level of the first enzyme electrode to the first substrate to be measured
- $A1, B1$: constants of calibration curve of the first enzyme electrode to the first substrate to be measured Likewise, from the concentrations and output levels in the second enzyme electrode, formula (5) (used as a second calibration curve for detecting the output level in the second enzyme electrode of the first substrate to be measured, as shown in FIG. 3 (2)) is obtained.

$$d2 = B2 \times c1 + A2 \tag{5}$$

where
- $c1$: concentration of the first substrate to be measured
- $d2$: output level of the second enzyme electrode attributed to the first substrate to be measured
- $A2, B2$: constants of calibration curve of the second enzyme electrode attributed to the first substrate to be measured Next, using a standard solution of the second substrate to be measured at known concentration ($c2$), the output level $d1$ attributable to the first substrate to be measured contained as an impurity is measured in the first enzyme electrode, and the output level $d23$ attributable to both the second substrate to be measured and the first substrate to be measured contained as an impurity is measured in the second enzyme electrode.

The contributing portion $d2'$ of the first substrate to be measured in the second enzyme electrode is obtained from formula (4) and (5) (see FIGS. 3 (1), (2)), $$d2' = \{B2 \times (d1' - A1)/B1\} + A2$$

and the contributing portion $d2'$ is subtracted from the output current $d23$ in the second enzyme electrode, thereby calculating $d3'$ as follows:

$$d3' = d23 - d2'$$

Similarly measuring standard solutions of the second substrate to be measured at several concentrations, formula (6) about the corrected output current and concentration (used as a third calibration curve for determination of second substrate to be measured, as shown in FIG. 3 (3)) is obtained.

$$d3' = B3' \times c2 + A3' \qquad (6)$$

where
- c2: concentration of the second substrate to be measured
- d3': true output level of the second enzyme electrode attributable to the second substrate to be measured
- A3', B3': constants of calibration curve of the second enzyme electrode to the second substrate to be measured Thus, the first, second and third calibration curves are plotted automatically, and are stored in first, second and third memories in the arithmetic processing unit. The calibration curves may be used in a certain small error range as long as the experimental conditions are not changed.

However, the enzymatic reaction changes its rate when the pH of the buffer solution is changed only slightly even if the temperature, sample volume and flow rate are constant. In actual measurement, considering conditions of the parts of the apparatus, for example, temperature fluctuations in the detecting unit due to ambient temperature or slight variation of the pump flow rate, it is desirable to calculate the calibration curve just before the measurement of the sample from the viewpoint of measuring at a high precision.

Incidentally, although different due to the capacity of the memory and purpose of use of the apparatus, it may be also possible to store the calibration curves for plural sets of objects of measurement, and select and use the proper calibration curves when the electrodes are exchanged. In this method, however, due caution is needed because the number of condition fluctuation factors may increase.

Determination means 2

A sample solution containing the first substrate to be measured and the second substrate to be measured, both of unknown concentrations, is measured by two enzyme electrodes, and the output level d1 attributable to the first substrate to be measured is obtained in the first enzyme electrode, and the output level d23 attributable to both the first substrate to be measured and the second substrate to be measured is obtained in the second enzyme electrode.

The concentration of the first substrate to be measured c1 is obtained by putting the output level d1 in the first enzyme electrode into formula (4) as shown below in formula (a).

$$c1 = (d1 - A1)/B1 \qquad (a)$$

Next, the concentration of the second substrate to be measured is obtained by first calculating the output level expected for the first substrate to be measured in the second enzyme electrode from the formula (5) as shown in formula (b) to be obtained as correction value d2. Then subtract this correction value d2 from the output level d23 obtained in the second enzyme electrode as shown in formula (c) to obtain d3 (the level purely attributable to the second substrate to be measured), and put this value in formula (6) as shown below in formula (d).

$$d2 = \{B2 \times (d1 - A1)/B1\} + A2 \qquad (b)$$

$$d3 = d23 - d2 \qquad (c)$$

$$c2 = (d3 - A3)/B3 \qquad (d)$$

The present invention apparatus was tested, by the amperometric measurement according to the Calibration means 2, using distilled water as a control sample and also using glucose standard solutions of 10, 20, 30 mmol/l, and sucrose standard solutions of 10, 20, 30 mmol/l. The apparatus was installed with the first enzyme electrode having immobilized glucose oxidase, and the second enzyme electrode having immobilized invertase, mutarotase and glucose oxidase. Afterwards, instead of using the solutions of unknown concentrations, using again the glucose standard solutions of 10, 20, 30 mmol/l and sucrose standard solutions of 10, 20, 30 mmol/l, each measurement was repeated three times according to the Determination means 2, and the results are shown below in Table 1.

Besides, by way of comparison, the results of measurement according to the Calibration means 1 and Determination means 1 which lacks correction of the calibration curve of the second substrate to be measured are shown below in Table 2.

As known from Table 1 and 2, in the measurement employing the two-substrate measuring apparatus of the invention, the error of the determination of the second substance to be measured has been notably improved.

TABLE 1

| Substance measured | Results of measurement (Unit: mmol/l) | | | | | |
|---|---|---|---|---|---|---|
| | Glucose | | | Sucrose | | |
| | 1st | 2nd | 3rd | 1st | 2nd | 3rd |
| 10 mmol/l glucose | 10.12 | 9.85 | 9.8 | 0.02 | 0.35 | 0.40 |
| 20 mmol/l glucose | 20.15 | 19.97 | 19.89 | 0.00 | 0.11 | 0.37 |
| 30 mmol/l glucose | 30.16 | 29.94 | 29.73 | 0.00 | 0.00 | 0.00 |
| 10 mmol/l sucrose | 0.39 | 0.37 | 0.33 | 10.18 | 9.99 | 9.88 |
| 20 mmol/l sucrose | 0.78 | 0.79 | 0.75 | 20.08 | 19.91 | 19.59 |
| 30 mmol/l sucrose | 0.65 | 0.68 | 0.68 | 29.75 | 30.34 | 30.00 |

TABLE 2

| Substance measured | Results of measurement (Unit: mmol/l) | | | | | |
|---|---|---|---|---|---|---|
| | Glucose | | | Sucrose | | |
| | 1st | 2nd | 3rd | 1st | 2nd | 3rd |
| 10 mmol/l glucose | 10.12 | 9.85 | 9.81 | 0.00 | 0.15 | 0.19 |
| 20 mmol/l glucose | 20.15 | 19.97 | 19.89 | 0.00 | 0.00 | 0.16 |
| 30 mmol/l glucose | 30.16 | 29.94 | 29.73 | 0.00 | 0.00 | 0.00 |
| 10 mmol/l sucrose | 0.39 | 0.37 | 0.33 | 9.65 | 9.46 | 9.36 |
| 20 mmol/l sucrose | 0.78 | 0.79 | 0.75 | 19.21 | 19.05 | 20.01 |
| 30 mmol/l sucrose | 0.65 | 0.68 | 0.68 | 29.46 | 29.14 | 28.81 |

The invention has been hitherto mainly illustrated in the measurement of a sucrose and glucose coexistent system, but the invention also brings about similar effects by using appropriate enzyme electrodes even in simultaneous measurement of two substrates using enzyme electrodes producing the same electrode active substance by the same final enzymatic reactions in a maltose and glucose coexistent system, an esterified and free cholesterol coexistent system, and others.

That is, if the first substrate is glucose and the second substrate is sucrose, the first enzyme electrode is an electrode having immobilized glucose oxidase, and the second enzyme electrode is an electrode having immobilized glucose oxidase, mutarotase and invertase, as stated above.

Besides, if the first substrate is glucose and the second substrate is maltose, the first enzyme electrode is an electrode having immobilized glucose oxidase, and the second enzyme electrode is an electrode having immobilized glucose oxidase, mutarotase and α-glucoxidase.

If the first substrate is glucose and the second substrate is β-glucoside, the first enzyme electrode is an electrode having immobilized glucose oxidase, and the second enzyme electrode is an electrode having immobilized glucose oxidase and β-glucosidase.

If the first substrate is glucose and the second substrate is maltooligosugars, the first enzyme electrode is an electrode having immobilized glucose oxidase, and the second enzyme electrode is an electrode having immobilized glucose oxidase and glucoamylase.

If the first substrate is glucose and the second substrate is lactose, the first enzyme electrode is an electrode having immobilized glucose oxidase, and the second enzyme electrode is an electrode having immobilized glucose oxidase and lactase.

For detection of free cholesterol and esterified cholesterol, the first enzyme electrode is an electrode having immobilized cholesterol oxidase, and the second enzyme electrode is an electrode having immobilized cholesterol oxidase and cholesterol esterase.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An apparatus for measuring the concentration of a substrate A and a substrate B in a solution, said apparatus comprising:
   a. a first enzyme electrode for responding only to said substrate A;
   b. a second enzyme electrode for responding to both said subtrate A and said substrate B, each of said electrodes in contact with the solution containing substrates A and/or B and each of said electrodes comprising a conductive base and immobilized enzyme which catalyzes a reaction for forming a detectable substance and for providing an output level corresponding thereto;
   c. a first memory for storing a first calibration curve for expressing the relationship between the concentration of said substrate A and said output level of said first enzyme electrode;
   d. a second memory for storing a second calibration curve for expressing the relationship between the concentration of said substrate A and said output level of said second enzyme electrode;
   e. a first programmable processing means and a third memory for storing a third calibration curve for expressing the relationship between the concentration of said substrate B and the output level of said second enzyme electrode calculated by said processing means;
   f. said first processing means being programmed for calculating said third calibration curve on the basis of the output levels of said second enzyme electrode of said subtrate B obtained by changing the concentration of said substrate B in standard solutions, and repeating the programmed processing in the following sequence of f1 to f5;

f1. detecting the output levels attributable to a standard solution in said first enzyme electrode and said second enzyme electrode, wherein said standard solution contains said substrate A and said substrate B with a known concentration of said substrate B;
   f2. determining the concentration of said substrate A on the basis of the detected output level in said first electrode and said first calibration curve stored in said first memory;
   f3. determining the output level in said second enzyme electrode of said substrate A on the basis of the calculated concentration of said substrate A and said second calibration curve stored in said second memory;
   f4. calculating the output level in said second enzyme electrode of said substrate B by subtracting the calculated output level in said second enzyme electrode of said substrate A obtained in step f3 from the output level in said second enzyme electrode of said standard solution;
   f5. calculating a relationship between the output level obtained in step f4 and the concentration of said substrate B;
   g. a second programmable means for calculating the concentrations of said substrate A and substrate B in a sample solution using said first, second and third calibration curves;
   the second processing means effecting the following programmed processing sequences:
   g1. calculating a concentration C1 of the substrate A in the sample on the basis of the first calibration curve and an output level d1 of the first enzyme electrode with respect to the sample;
   g2. calculating a contribution output level d2 of the concentration of the substrate A in the second enzyme electrode on the basis of the concentration C1 of the substrate A and the second calibration curve; and calculating a balance d3 by subtracting d2 from an output level d23 of the second enzyme electrode with respect to the sample; and calculating a concentration C2 of the substrate B on the basis of the balance d3 and the third calibration curve.

2. An apparatus according to claim 1, wherein a solution flows between said first and second enzyme electrodes and wherein said second enzyme electrode is disposed at a downstream side of said first enzyme electrode;
   said apparatus further comprising:
   a sample injection means disposed upstream of said first electrode for injecting a sample into said flowing solutions said second enzyme electrode is disposed at a downstream side of first enzyme electrode;
   a mixing coil disposed between said first enzyme electrode and said second enzyme electrode for diffusing and diluting said substrate A and substrate B in said flowing solution.

3. An apparatus for measuring the concentration of a substrate A and a substrate B in a solution, said apparatus comprising:
   a. a first enzyme electrode for responding only to said substrate A;
   b. a second enzyme electrode for responding to both said substrate A and said substrate B, each of said electrodes in contact with the solution containing substrates A and/or B and each of said electrodes comprising a conductive base and immobilized enzyme which catalyzes a reaction for forming a detectable substance and for providing an output level corresponding thereto;

c. a first memory for storing a first calibration curve for expressing the relationship between the concentration of said substrate A and said output level of said first enzyme electrode;

d. a second memory for storing a second calibration curve for expressing the relationship between the concentration of said substrate A and said output level of said second enzyme electrode;

e. a first programmable processing means and a third memory for storing a third calibration curve for expressing the relationship between the concentration of said substrate B and the output level of said second enzyme electrode calculated by said processing means;

f. said first processing means being programmed for calculating said third calibration curve on the basis of the output levels of said second enzyme electrode of said substrate B obtained by changing the concentration of said substrate B in standard solutions, and repeating the programmed processing in the following sequence of f1 to f4;

f1. detecting the output levels attributable to a standard solution in said first enzyme electrode and said second enzyme electrode, wherein said standard solution contains said substrate A and said substrate B with a known concentration of said substrate B;

f2. determining the concentration of said substrate A on the basis of the detected output level in said first electrode and said first calibration curve stored in said first memory;

f3. determining the output level in said second enzyme electrode of said substrate A on the basis on the calculated concentration of said substrate A and said second calibration curve stored in said second memory;

f4. calculating the output level in said second enzyme electrode of said substrate B by subtracting the calculated output level in said second enzyme electrode of said substrate A from the output level in said second enzyme electrode of said standard solution; and g. a second processing means being programmed for calculating the concentrations of said substrate A and substrate B in a solution using said first, second and third calibration curves.

4. A method of measuring the concentration of a substrate A and a substrate B in a solution, using a first enzyme electrode for responding only to the substrate A, and a second enzyme electrode for responding to both substrate A and substrate B, said method comprising:

(1) a step of calculating a first calibration curve for expressing a relationship between the concentration of substrate A and an output level of the first enzyme electrode by measuring a plurality of standard solutions of substrate A using the first enzyme electrode;

(2) a step of calculating a second calibration curve for expressing a relationship between the concentration of substrate A and an output level of the second enzyme electrode by measuring a plurality of standard solutions of substrate A using the second enzyme electrode;

(3) a step of calculating a third calibration curve for expressing the relationship between the concentration of substrate B and the output level of the second enzyme electrode, by:

(3.1) determining the concentration of substrate A contained in the standard solution of B which contains an unknown amount of substrate A as impurities by measuring the output level of the first enzyme electrode with respect to the standard solution of B and the first calibration curve;

(3.2) determining the output level of the second enzyme electrode of substrate A contained in the standard solution of B by using the concentration of substrate A obtained in step (3.1) and the second calibration curve;

(3.3) determining the output level of the second enzyme electrode of substrate B, by subtracting the output level of the second enzyme electrode of substrate A obtained in step (3.2) from the output level of the second enzyme electrode measuring the standard solution of B;

(3.4) calculating a relationship between the concentration of the standard solution of B and the output level of the second enzyme electrode of substrate B obtained in step (3.3);

(4) a step of determining the concentrations of substrate A and substrate B in a sample comprising the steps of:

(4.1) determining a concentration C1 of the substrate A in the sample on the basis of the first calibration curve and an output level d1 measured by the first enzyme electrode;

(4.2) determining an output level d2 of substrate A in the second enzyme electrode using the concentration C1 of the substrate A and the second calibration curve; and calculating a balance d3 by subtracting d2 from an output level d23 of the second enzyme electrode with respect to the sample; and calculating a concentration C2 of the substrate B on the basis of the balance d3 and the third calibration curve.

* * * * *